United States Patent
Lastimado et al.

(10) Patent No.: US 11,141,119 B1
(45) Date of Patent: Oct. 12, 2021

(54) DENTAL IMPLANT X-RAY HOLDING DEVICE

(71) Applicants: Marcus Lastimado, Murphy, TX (US); Trinity Lam-Lastimado, Murphy, TX (US)

(72) Inventors: Marcus Lastimado, Murphy, TX (US); Trinity Lam-Lastimado, Murphy, TX (US)

(*) Notice: Subject to any disclaimer, the term of this patent is extended or adjusted under 35 U.S.C. 154(b) by 0 days.

(21) Appl. No.: 15/416,782

(22) Filed: Jan. 26, 2017

Related U.S. Application Data

(60) Provisional application No. 62/287,010, filed on Jan. 26, 2016.

(51) Int. Cl.
*A61B 6/14* (2006.01)
*A61C 8/00* (2006.01)

(52) U.S. Cl.
CPC ............ *A61B 6/145* (2013.01); *A61C 8/0089* (2013.01)

(58) Field of Classification Search
CPC .......... A61B 6/10; A61B 6/14; A61B 6/4283; A61B 6/145; G03B 42/04; G03B 42/042
USPC ................ 378/167, 168, 189, 191, 204, 205
See application file for complete search history.

(56) References Cited

U.S. PATENT DOCUMENTS 9,351,692 B2 * 5/2016 Yao .......................... A61B 6/14

* cited by examiner

*Primary Examiner* — Jurie Yun
(74) *Attorney, Agent, or Firm* — Cramer Patent & Design PLLC; Aaron R. Cramer

(57) ABSTRACT

A dental X-ray sensor holding device includes a rectangular sensor platform and a long handle having telescoping sections. The device holds and positions a purchased X-ray sensor within a patient's mouth during a dental procedure or during surgery. The long handle allows a dental professional to stand at a safe distance out of the X-ray radiation range.

20 Claims, 3 Drawing Sheets

DENTAL IMPLANT X-RAY HOLDING DEVICE

RELATED APPLICATIONS

This application claims the benefit of U.S. Provisional Application No. 62/287,010 which was filed Jan. 26, 2016, the entire disclosures of which are incorporated herein by reference.

FIELD OF THE INVENTION

The invention relates generally to a dental X-ray sensor holding device.

BACKGROUND OF THE INVENTION

When performing procedures that require X-rays as a dental professional, it is not only safe, but an Occupational Safety and Health Administration (OSHA) requirement to be a specific distance away from the X-ray machine. Certain procedures however require the use of an X-ray sensor that be must be held in a specific manner within a patient's mouth. This provides a conundrum: more control on the retention of the sensor in the patient's mouth may require the professional to be close to the patient, and thus the X-ray machine, but it may run afoul of OSHA regulations and it is an unsafe practice, particularly if repeatedly performed.

Accordingly, there exists a need for a holding device to enable a dental professional to stand at a safe distance out of the X-ray radiation range during an X-ray procedure. It is also a desire to have such a device be capable of adjustment, both in a longitudinal but also in a radial direction as all patient's mouths and procedures may require different orientations of the X-ray sensor. Such as device should also not interfere with the X-ray machine's operation.

SUMMARY OF THE INVENTION

The principles of the present invention provide for a sensor holder comprising of a handle assembly which has a handle assembly first end and a handle assembly second end and a sensor holder assembly which has a sensor holder assembly first end that is pivotally attached to the handle assembly second end and a sensor holder assembly second end. The sensor holder assembly is capable of securing a digital X-ray sensor while the handle assembly has an adjustable length capable of extending and retracting the sensor holder assembly a distance away from or toward the handle assembly end first. An alternate embodiment of the sensor holder may comprise of a handle assembly also having a plurality of telescoping sections. With respect to this configuration, the number of telescoping sections may be further limited to three (3).

With respect to the preferred embodiment, the handle assembly may comprise of a grip which is located at the handle assembly first end and a plurality of telescoping sections arranged in a linear manner, secured superjacent the grip and terminating while also being located at the handle assembly second end. The plurality of telescoping sections has successively decreasing diameters with a largest diameter of the telescoping sections being secured superjacent the grip and a smallest the telescoping sections being secured subjacent the sensor holder assembly first end. The telescoping sections are slip-fitted and nested within an internal cavity of each immediately adjacent telescoping section.

The handle assembly second end may also comprise of a T-connector having an internal lengthwise aperture through a top portion thereof. The grip may further comprise of a cylindrical extruded layer of a high-friction material. The plurality of telescoping sections can collapse to a length of no less than one foot (1 ft.) or extending to a length of no more than seven feet (7 ft.).

The sensor holder assembly may also comprise of a C-shaped pivot block which is pivotally secured to the handle assembly second end while having a first aperture through a first arm and a second aperture partially through a second arm, a sensor platform located at the sensor holder assembly second end and an arm interconnecting the pivot block and the sensor platform. The second aperture is aligned with the first aperture. The sensor platform is capable of removably securing a digital X-ray sensor.

The sensor holder may also comprise of a pivot bolt and a tightening knob which is secured to a first end of the pivot bolt. The pivot bolt is capable of being secured within the "C"-shaped pivot block first aperture, the "T"-connector aperture and the "C"-shaped pivot block second aperture when the "T"-connector is placed between the "C"-shaped pivot block and aligned. The sensor platform may be securable at a selectable angle along one (1) axis relative to the handle assembly. The arm may also comprise of a generally semi-circular-shaped recessed edge along a first side thereby permitting placement of the sensor holder assembly in a posterior area of a mouth of a user while providing clearance with teeth of the user. The sensor platform may further comprise of a pair of side guide rails each being secured on a first face of the sensor platform on opposite widthwise sides and an end guide rail secured on the first face of the sensor platform at a bottom lengthwise side. The pair of the side guide rails and the end guide rail are capable of removably retaining corresponding edge portions of the digital X-ray sensor.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

| DESCRIPTIVE KEY | |
|---|---|
| 10 | dental implant X-ray holder |
| 20 | sensor holder assembly |
| 22 | arm |
| 24 | sensor platform |
| 26 | side guide rail |
| 28 | end guide rail |
| 30 | recessed edge |
| 50 | handle assembly |

-continued

| | DESCRIPTIVE KEY |
|---|---|
| 52a | first telescoping section |
| 52b | second telescoping section |
| 52c | third telescoping section |
| 54 | grip |
| 56 | "T"-connector |
| 60 | pivot block |
| 62 | slot |
| 63 | pivot bolt |
| 64 | tightening knob |
| 66 | threaded region |
| 100 | X-ray sensor |
| 110 | sensor signal wire |

DETAILED DESCRIPTION OF THE PREFERRED EMBODIMENT

Figure 1:
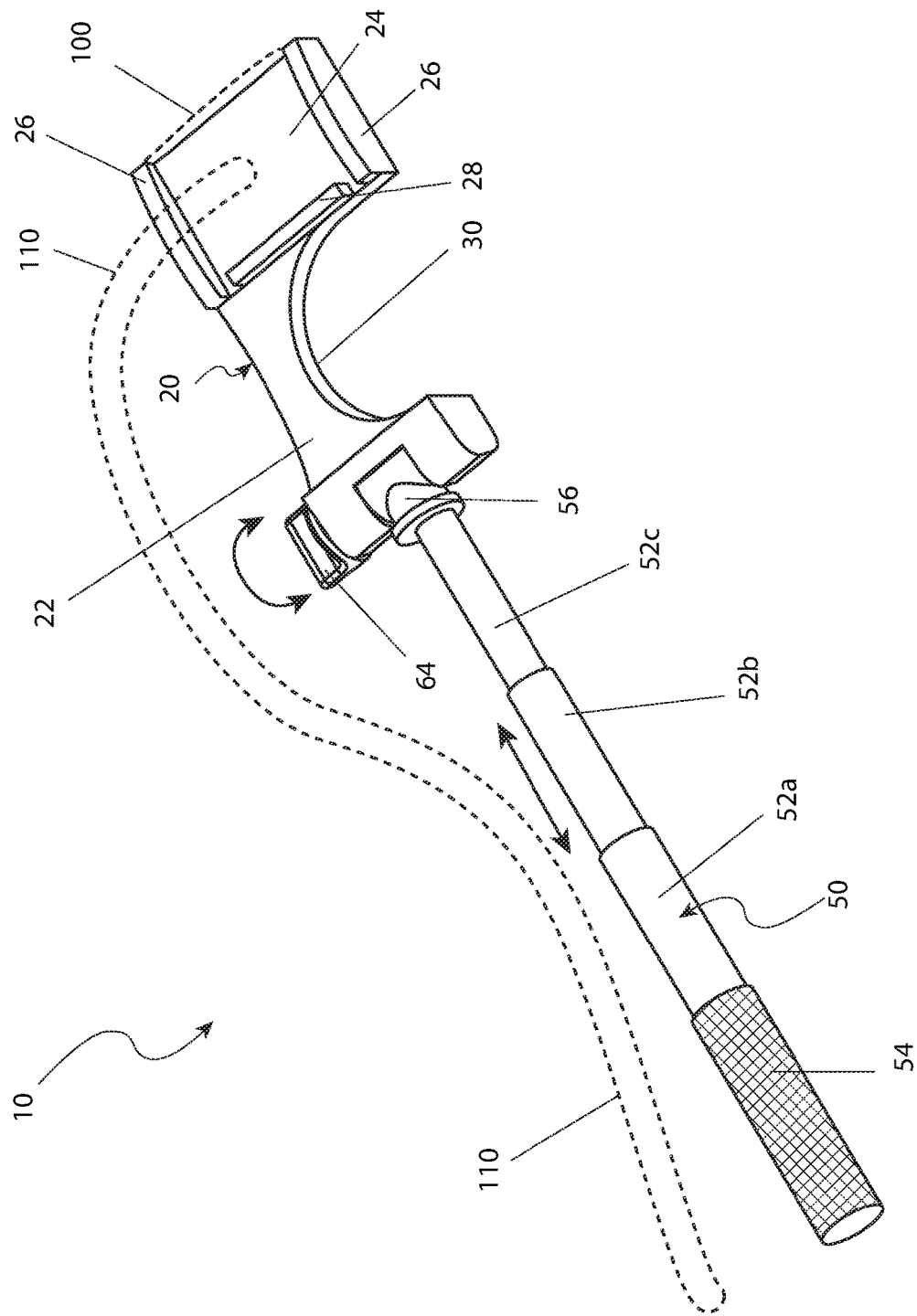
FIG. 1 is a perspective view of a dental implant X-ray holding device 10, according to a preferred embodiment of the present invention.
Figure 2:
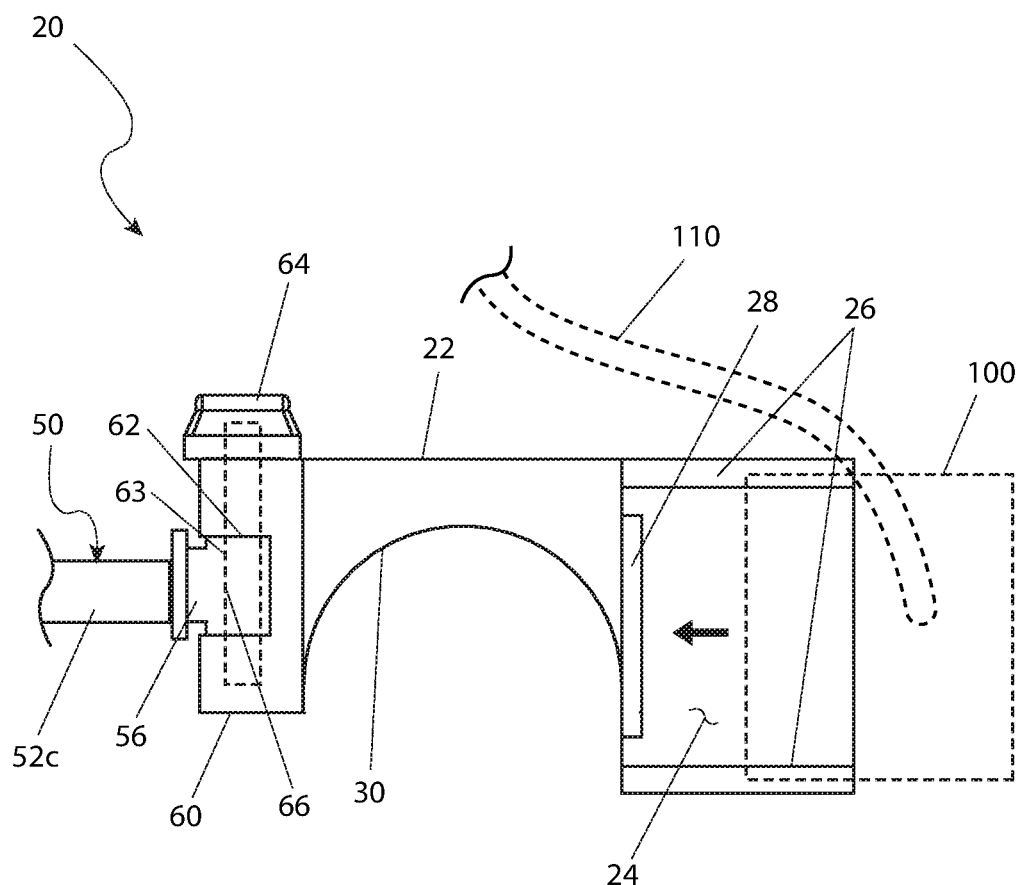
FIG. 2 is a top close-up view of a sensor holder assembly portion 20 of the dental implant X-ray holding device 10, according to a preferred embodiment of the present invention.
Figure 3:
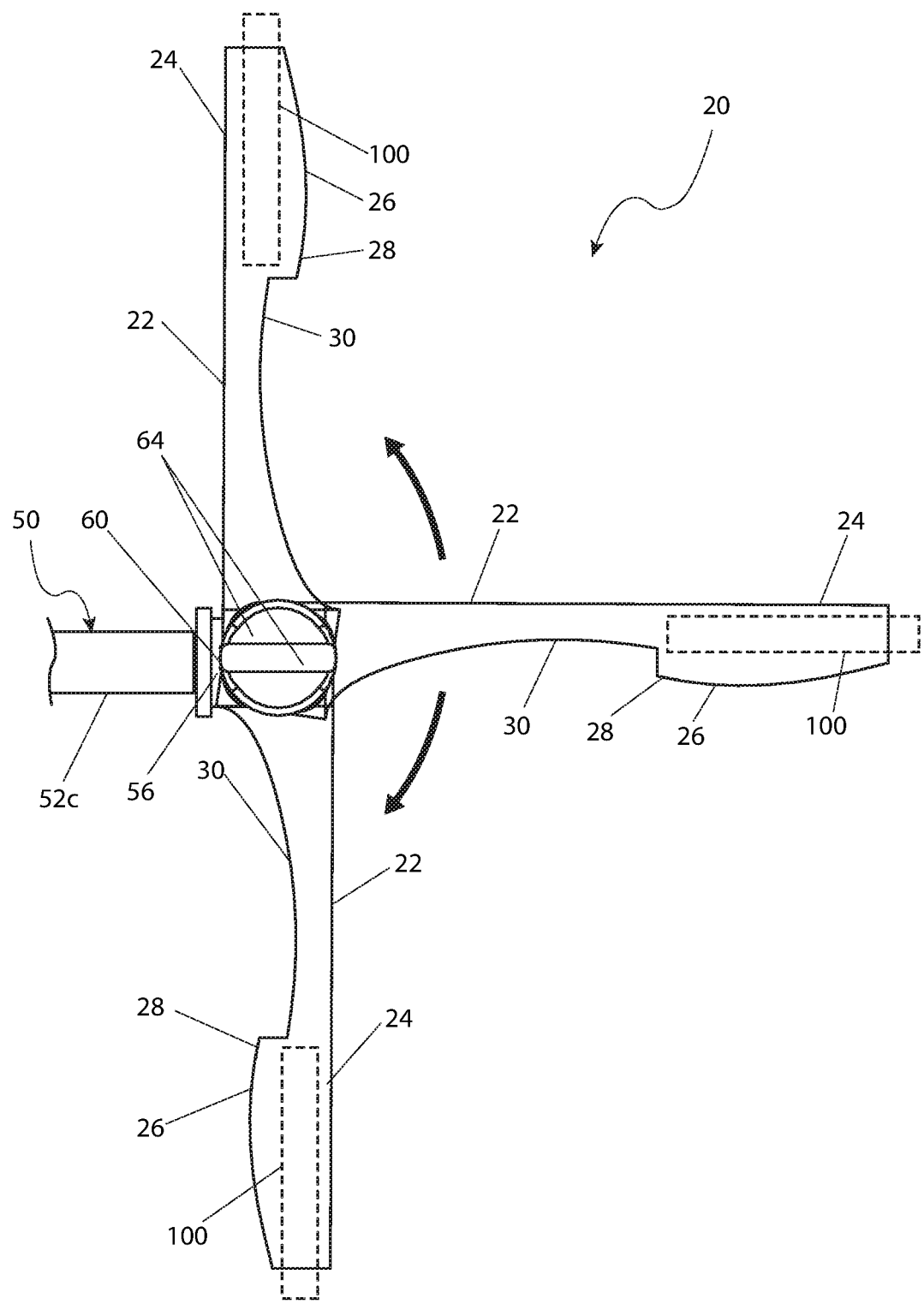
FIG. 3 is a side close-up view of the sensor holder assembly portion 20 of the dental implant X-ray holding device 10 depicting rotation of a pivot block portion 60, according to a preferred embodiment of the present invention.

The best mode for carrying out the invention is presented in terms of its preferred embodiment, herein depicted within FIG. 1 through 3. However, the invention is not limited to the described embodiment, and a person skilled in the art will appreciate that many other embodiments of the invention are possible without deviating from the basic concept of the invention and that any such work around will also fall under scope of this invention. It is envisioned that other styles and configurations of the present invention can be easily incorporated into the teachings of the present invention, and only one (1) particular configuration shall be shown and described for purposes of clarity and disclosure and not by way of limitation of scope.

The terms "a" and "an" herein do not denote a limitation of quantity, but rather denote the presence of at least one (1) of the referenced items.

The present invention describes a dental implant X-ray holder (herein described as the "device") 10, which provides a means to hold and accurately position an existing dental X-ray sensor 100, within a patient's mouth during a dental procedure. The device 10 includes a rectangular sensor holder assembly 20 and a telescoping handle assembly 50. The X-ray sensor 100 is envisioned to be an existing purchased digital dental X-ray sensor 100 such as those manufactured by Suni Medical Imaging®, SOTA Imaging®, and other companies which manufacture such products.

Referring now to FIG. 1, a perspective view of the device 10, according to the preferred embodiment of the present invention, is disclosed. The device 10 enables a dental surgeon, dentist, or assistant to position and hold a digital dental X-ray sensor 100 in a patient's mouth during a dental procedure such as, but not limited to, dental implant surgery. When used in conjunction with the existing purchased digital X-ray sensor 100, the device 10 enables a continuous feed of digital data from a dental procedure site for viewing upon a display and/or performing video capture. The existing digital X-ray sensor 100 is envisioned to be of a standard size and shape and having an integral extending sensor signal wire 110 being routed to, and in electrical communication with, a peripheral X-ray signal processing equipment (not shown). The device 10 includes a proximal length-adjustable handle assembly 50, being attached at a distal end portion to the sensor holder assembly 20.

The handle assembly 50 creates a distance between a dental professional and X-ray emitting equipment, thereby allowing the dental professional to stand at a safe distance from the X-ray sensor 100 and associated X-ray equipment. The device 10 enables the dental professional to be outside of a radiation range, so as to reduce or eliminate X-ray exposure. While holding a grip portion 54 of the handle assembly 50, the dental professional may position the sensor holder assembly 20 within the patient's mouth using a single hand.

The handle assembly 50 provides length-adjustable telescoping tubular sections 52a, 52b, 52c arranged in a linear manner and having successively decreasing diameters. An embodiment of the handle assembly 50 is shown here having a proximal first telescoping section 52a, an intermediate second telescoping section 52b, and a distal third telescoping section 52c. A cylindrical grip 54, preferably made using an extruded layer of a high-friction material such as rubber, is to be permanently affixed using an adhesive or equivalent method to an external surface portion of the first telescoping section 52a. It is envisioned that the device 10 would be made available in various models having different numbers of telescoping sections 52a, 52b, 52c, thereby being capable of extending from a minimum collapsed length of approximately one foot (1 ft.) in length, up to approximately seven feet (7 ft.) in length, thereby complying with OSHA standards for radiation exposure reduction. The telescoping sections 52a, 52b, 52c are envisioned to be made using materials such as, but not limited to: aluminum, injection moldable high temperature plastic, or the like. The handle assembly 50 is to provide overall length adjustability via a slip-fit connection between adjacent pairs of telescoping sections 52a, 52b, 52c. A friction force produced between the pairs of telescoping sections 52a, 52b, 52c allows a dental professional to select a particular desired length of the handle assembly 50, within a given range, as defined by an included number of telescoping sections 52a, 52b, 52c.

Referring now to FIGS. 2 and 3, close-up views of the sensor holder assembly portion 20 the device 10, according to the preferred embodiment of the present invention, are disclosed. The previously described handle assembly 50 is pivotingly affixed to the sensor holder assembly 20 via a "T"-connector 56 and a pivot block 60, which in turn provide a means to manipulate the sensor holder assembly 20 and X-ray sensor 100 within the sensor platform 24. The sensor holder assembly 20 provides a unitary machined or molded structure providing portions including the pivot block 60, the sensor platform 24, and an interconnecting planar arm portion 22. The sensor holder assembly 20 is envisioned to be made using a sterilizable plastic or metal material.

The pivot block 60 provides pivoting attachment of the handle assembly 50 to the sensor holder assembly 20 so as to allow a dental professional to select a desired included angle between. The sensor holder assembly 20 provides single-axis rotation of the sensor holder assembly 20 and is to be capable of positioning the sensor holder assembly 20 in a variable manner with respect to the handle assembly 50 along an arc extending at least ninety degrees (90°) above and ninety degrees (90°) below the center of the handle assembly 50.

The pivot block 60 acts to join the handle assembly 50 to the sensor holder assembly 20. The pivot block 60 provides a "C"-shaped structure having a center slot feature 62 being machined or molded through, and being shaped so as to snuggly receive a "T"-shaped "T"-connector portion 56 of the handle assembly 50 within. The "T"-connector 56 is to be integral to, or threadingly affixed to, a distal end of the third telescoping section 52c of the handle assembly 50. A tightening knob portion 64 having an integral protruding pivot bolt portion 63, is to be inserted into the pivot block 60 and the inserted "T"-connector 56, thereby acting as an axle to enable relative single-axis rotation of the sensor holder assembly 20. The pivot bolt 63 also includes an intermediate threaded region portion 66. A dental professional may secure the sensor holder assembly 20 at a desired angle with respect to the handle assembly 50 via rotation of the tightening knob 64 and pivot bolt 63 portions due to the engagement of the threaded region portion 66 of the pivot bolt 63 with the "T"-connector 56. Once a dental professional has positioned the sensor assembly holder 20, the tightening knob 64 is rotated causing the threaded region 66 to jam the "T"-connector 56 and pivot block 60 portions together, thereby securing a position of the sensor assembly holder 20.

The arm portion 22 provides a planar structure which extends between the pivot block 60 and the sensor platform 24. The arm 22 is to include a generally semi-circular-shaped recessed edge portion 30 along one (1) side, to allow ease of placement of the sensor holder assembly 20 within a posterior area of a patient's mouth, and to provide clearance for a patient's cheek and/or teeth portions.

The sensor platform 24 provides features which act to securely hold the existing X-ray sensor 100 in position, including a pair of integrally-molded "L"-shaped side guide rails 26 and a rectangular upwardly protruding end guide rail 28. The side 26 and end 28 guide rails are envisioned to be integrally-molded into respective edges of the sensor platform 24, thereby guiding, positioning, and securing three (3) corresponding edge portions of the rectangular X-ray sensor 100. The X-ray sensor 100 is envisioned to be secured within the side 26 and against the end 28 guide rail portions via a friction-fit of the X-ray sensor 100 between the parallel and opposing side guide rails 26. It is understood that other retaining features and devices may be integrated into the design of the sensor platform 24 to hold the X-ray sensor 100 in position such as, but not limited to: molded-in interfering protrusions, grooves or slots, spring clips, and the like, and as such should not be interpreted as a limiting factor of the device 10.

It is envisioned that other styles and configurations of the present invention can be easily incorporated into the teachings of the present invention, and only one particular configuration shall be shown and described for purposes of clarity and disclosure and not by way of limitation of scope.

The preferred embodiment of the present invention can be utilized by a dental professional in a simple and effortless manner with minimal training. After initial purchase or acquisition of the device 10, it would be installed as indicated in FIG. 1.

The method of utilizing the device 10 may be achieved by performing the following steps: procuring a model of the device 10 which includes a desired number of telescoping sections 52a, 52b, 52c; loading and securing an existing X-ray sensor 100 into the sensor holder assembly 20 by inserting the X-ray sensor 100 completely within the guide rail portions 26, 28 of the sensor platform 24 until a forward edge of the X-ray sensor 100 contacts the end guide rail 28; being careful that the sensor signal wire portion 110 of the X-ray sensor 100 extends in a desired direction; pivoting the sensor holding assembly 20 in relation to the handle assembly 50 to a desired angle; securing the angle of the sensor holder assembly 20 by rotating the tightening knob portion 64 of the pivot block 60 until tight; extending the telescoping sections 52a, 52b, 52c of the handle assembly 50 outwardly until obtaining a desired overall length of the handle assembly 50 to ensure a safe radiation condition for the dental professional; grasping the grip portion 54 of the handle assembly 50; inserting the sensor holder assembly portion 20 of the device 10 into the patient's mouth; allowing the recessed edge portion 30 of the arm 22 to provide clearance for mouth and teeth portions of the patient; manipulating the device 10 until obtaining a suitable position of the X-ray sensor 100 for acquiring X-ray images of the dental procedure site within the patient's mouth; allowing the patient, as needed, to help maintain the position of the X-ray sensor 100; acquiring X-ray image data or video data as needed during a dental procedure or surgical session; and, benefiting from a safe and easily manipulated X-ray acquiring device 10, afforded a user of the present invention 10.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated.

The invention claimed is:

1. A sensor holder, comprising:
  a handle assembly having a handle assembly first end and a handle assembly second end; and,
  a sensor holder assembly having a sensor holder assembly first end pivotally attached to said handle assembly second end and a sensor holder assembly second end;
  wherein said sensor holder assembly is capable of securing a digital X-ray sensor therein; and,
  wherein said handle assembly has an adjustable length capable of extending and retracting said sensor holder assembly a distance away from or toward said handle assembly first end.

2. The sensor holder of claim 1, wherein said handle assembly further comprises:
  a grip located at said handle assembly first end; and,
  a plurality of telescoping sections arranged in a linear manner, secured superjacent said grip and terminating and located at said handle assembly second end;
  wherein said plurality of telescoping sections have successively decreasing diameters with a largest diameter of said telescoping sections being secured superjacent said grip and a smallest said telescoping sections being secured subjacent said sensor holder assembly first end; and,
  wherein said telescoping sections are slip-fitted and nested within an internal cavity of each immediately adjacent telescoping section.

3. The sensor holder of claim 2, wherein said handle assembly second end further comprises a T-connector having an internal lengthwise aperture through a top portion thereof.

4. The sensor holder of claim 2, wherein said grip further comprises a cylindrical extruded layer of a high-friction material.

5. The sensor holder of claim 2, wherein said plurality of telescoping sections are capable of collapsing to a length of no less than one foot.

6. The sensor holder of claim 2, wherein said plurality of telescoping sections are capable of extending to a length of no more than seven feet.

7. The sensor holder of claim 1, wherein said sensor holder assembly further comprises:
  a C-shaped pivot block pivotally secured to said handle assembly second end having a first aperture through a first arm thereof and a second aperture partially through a second arm thereof, said second aperture aligned with said first aperture;

a sensor platform located at said sensor holder assembly second end; and, an arm interconnecting said pivot block and said sensor platform;

wherein said sensor platform is capable of removably securing said digital X-ray sensor therein.

8. The sensor holder of claim 7, further comprising:
a pivot bolt; and,
a tightening knob secured to a first end of said pivot bolt;
wherein said pivot bolt is capable of being secured within said C-shaped pivot block first aperture, a T-connector aperture and said C-shaped pivot block second aperture when said T-connector is placed between said C-shaped pivot block and aligned therewith; and,
wherein said sensor platform is securable at a selectable angle along one axis relative to said handle assembly.

9. The sensor holder of claim 7, wherein said arm comprises a generally semi-circular-shaped recessed edge along a first side;
wherein said arm is capable of permitting placement of said sensor holder assembly in a posterior area of a mouth of a user while providing clearance with teeth of said user.

10. The sensor holder of claim 7, wherein said sensor platform further comprises:
a pair of side guide rails each secured on a first face of said sensor platform on opposite widthwise sides thereof; and,
an end guide rail secured on said first face of said sensor platform at a bottom lengthwise side thereof;
wherein said pair of said side guide rails and said end guide rail are capable of removably retaining corresponding edge portions of said digital X-ray sensor.

11. A sensor holder, comprising:
a handle assembly having a handle assembly first end, a handle assembly second end and a plurality of telescoping sections between said handle assembly first end and said handle assembly second end; and,
a sensor holder assembly having a sensor holder assembly first end pivotally attached to said handle assembly second end and a sensor holder assembly second end;
wherein said sensor holder assembly is capable of securing a digital X-ray sensor therein; and,
wherein said handle assembly has an adjustable length capable of extending and retracting said sensor holder assembly a distance away from or toward said handle assembly first end.

12. The sensor holder of claim 11, wherein said handle assembly further comprises a grip comprising said handle assembly first end;
wherein said plurality of telescoping sections is limited to three said telescoping sections arranged in a linear manner, secured superjacent said grip and terminating and comprising said handle assembly second end;
wherein each said telescoping section have successively decreasing diameters with a largest diameter of said telescoping sections being secured superjacent said grip and a smallest said telescoping sections being secured subjacent said sensor holder assembly first end; and,
wherein each successive said telescoping section proceeding from said grip to said handle assembly second end are slip-fit and nest within an internal cavity of each immediately adjacent said telescoping section.

13. The sensor holder of claim 12, wherein said handle assembly second end further comprises a T-connector having an internal lengthwise aperture through a top portion thereof.

14. The sensor holder of claim 12, wherein said grip further comprises a cylindrical extruded layer of a high-friction material.

15. The sensor holder of claim 12, wherein said plurality of telescoping sections are capable of collapsing to a length of no less than one foot.

16. The sensor holder of claim 12, wherein said plurality of telescoping sections are capable of extending to a length of no more than seven feet.

17. The sensor holder of claim 11, wherein said sensor holder assembly further comprises:
a C-shaped pivot block pivotally secured to said handle assembly second end having a first aperture through a first arm thereof and a second aperture partially through a second arm thereof, said second aperture aligned with said first aperture;
a sensor platform located at said sensor holder assembly second end; and,
an arm interconnecting said pivot block and said sensor platform;
wherein said sensor platform is capable of removably securing said digital X-ray sensor therein.

18. The sensor holder of claim 17, further comprising:
a pivot bolt; and,
a knob secured to a first end of said pivot bolt;
wherein said pivot bolt is capable of being secured within said C-shaped pivot block first aperture, a T-connector aperture and said C-shaped pivot block second aperture when said T-connector is placed between said C-shaped pivot block and aligned therewith; and,
wherein said sensor platform is securable at a selectable angle along one axis relative to said handle assembly.

19. The sensor holder of claim 17, wherein said arm comprises a generally semi-circular-shaped recessed edge along a first side;
wherein said arm is capable of permitting placement of said sensor holder assembly in a posterior area of a mouth of a user while providing clearance with teeth of said user.

20. The sensor holder of claim 17, wherein said sensor platform further comprises:
a pair of side guide rails each secured on a first face of said sensor platform on opposite widthwise sides thereof; and,
an end guide rail secured on said first face of said platform at a bottom lengthwise side thereof;
wherein said pair of said side guide rails and said end guide rail are capable of removably retaining corresponding edge portions of said digital X-ray sensor.

* * * * *